US00PP16269P3

(12) United States Plant Patent
Dodd, III et al.

(10) Patent No.: US PP16,269 P3
(45) Date of Patent: Feb. 21, 2006

(54) **VARIEGATED *ILLICIUM***

(50) Latin Name: *Illicium floridanum*
Varietal Denomination: Gaddy

(76) Inventors: Thomas H. Dodd, III, Post Office Drawer 439, Semmes, AL (US) 36575; Thayre Dodd, Post Office Drawer 439, Semmes, AL (US) 36575

( * ) Notice: Subject to any disclaimer, the term of this patent is extended or adjusted under 35 U.S.C. 154(b) by 235 days.

(21) Appl. No.: 10/918,168

(22) Filed: Aug. 13, 2004

(65) Prior Publication Data

US 2005/0044599 P1 Feb. 24, 2005

Related U.S. Application Data

(63) Continuation of application No. 10/156,357, filed on May 28, 2002.

(51) Int. Cl.
*A01H 5/00* (2006.01)

(52) U.S. Cl. ..... Plt./226

(58) Field of Classification Search ..... Plt./226
See application file for complete search history.

*Primary Examiner*—Bruce R. Campell
*Assistant Examiner*—S. B. McCormick-Ewoldt
(74) *Attorney, Agent, or Firm*—Alston & Bird LLP

(57) ABSTRACT

A new and distinct form of *Illicium* plant, characterized by its pink flowers are variegated leaves.

4 Drawing Sheets

Latin name of the genus and species of the plant claimed: *Illicium floridanum* J. Ellis *forma variegatum* Gaddy is a pink-flowered, variegated-leaved form of *Illicium floridanum* (star-anise, Florida anise).

BACKGROUND OF THE INVENTION

The present invention relates to a new and distinct form of *Illicium floridanum,* referred to commercially as a Variegated *Illicium.*

This invention has produced a new variegated-leaved form of *Illicium floridanum forma variegatum.* It was propagated by shoot from *Illicium floridanum forma albiflorum* 'Semmes,' a white-flowered nonvariegated-leaved form of *Illicium floridanum. Illicium floridanum* J. Ellis *forma variegatum* Gaddy is an *Illicium* having variegated leaves and a light pink flower from the form of *Illicium floridanum* (star-anise, Florida anise).

Table 1 gives data on various taxonomic characters of the new form and typical *floridanum.* Characters seen in young plants of *Illicium floridanum forma variegatum* not mentioned in the description of typical *Illicium floridanum* (Vincent in Flora of North America, 1997) include asymmetrical leaves, curved leaf tips (apices), pink flower color, and leaf variegation. Differt a *Illicium floridanum* J. Ellis *foliis variegatis et floribus roseus.* (Differs from *Illicium floridanum* J. Ellis by its variegated leaves and by its pink flowers.). In container-grown plants less than 0.5 meter tall, leaves were significantly smaller than those of typical *Illicium floridanum;* however, this difference may be due to the fact that these plants are young shoots. It was propagated by shoot from *Illicium floridanum* 'Alba', variety 'Semmes,' a white-flowered nonvariegated-leaved form of *Illicium floridanum.*

This invention has not been observed under all possible environmental conditions. The phenotype may vary significantly with variations in environment such as temperature, light intensity, and day length, without, however, any variation in genotype.

SUMMARY OF THE INVENTION

This new variety is endowed with a unique combination of traits which are determined to be the basic characteristics of this invention which in combination distinguish it as new and distinct, and materially contributes to its attractiveness. Among its important and dominant characteristics are the following: (1) the leaves of the new variety are variegated having a gray-green color at the exterior edges of the leaf and ranging from to a yellow-green to yellow at the interior of the leaf; and (2) the flowers of the new variety are light pink with the inner petals fading to a softer pink.

This invention is best compared to wild *floridanum.* A comparison for the leaf and flower characteristics is shown in Table 1 wherein it can be seen that the leaves both as to size and shape are distinct. Also, the flower color is distinct from the wild *floridanum.* The plant was 5 years old when spontaneous mutation was found. That mutation is now 12 years old.

The flower color and leaf variegation of *forma variegatum* has remained stable in offshoots from the original variegated-leaved plant shows that the foregoing characteristics come true to form and are established and transmitted through succeeding propagation. The plant's winter hardiness is USDA zone 6 and the drought/heat tolerance is USDA zone 10.

BRIEF DESCRIPTION OF THE PHOTOGRAPHS

The accompanying photographs show specimens of the new variety, with their foliage and flowers in different stages of development.

Figure 1:
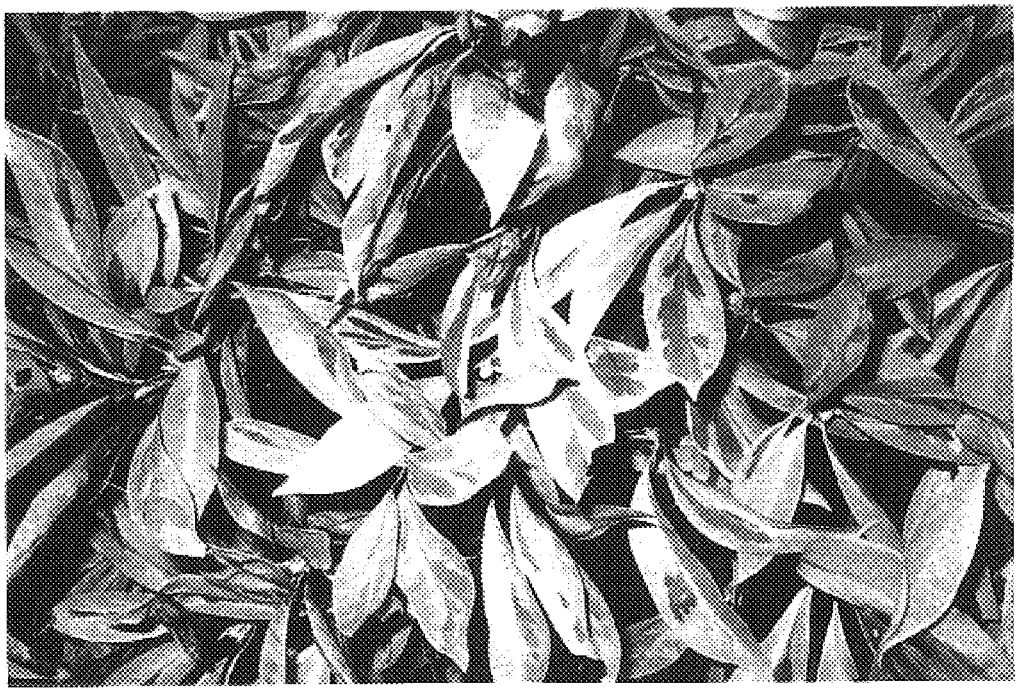
FIG. 1 is a close-up photograph illustrating the variegated leaves of the new plant.
Figure 2:
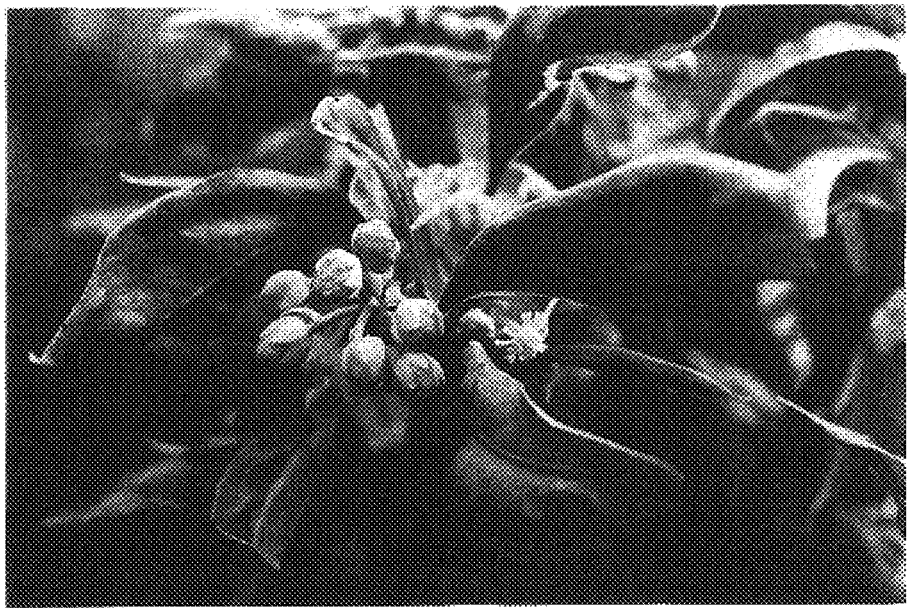
FIG. 2 is a photograph illustrating a cluster of buds of a typical plant.
Figure 3:
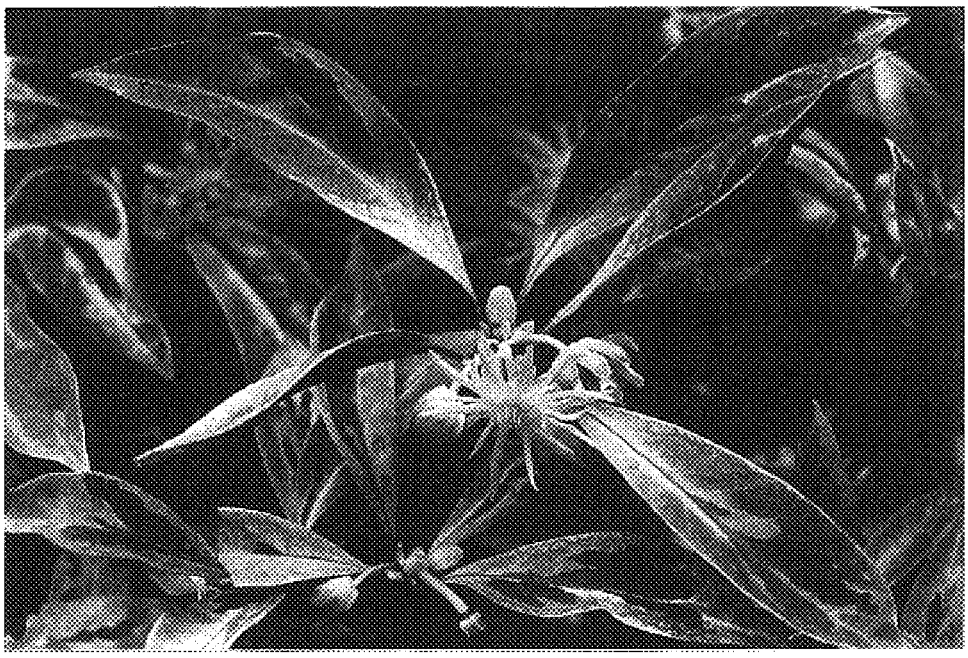
FIG. 3 is a photograph which illustrates a single flower of the new plant.
Figure 4:
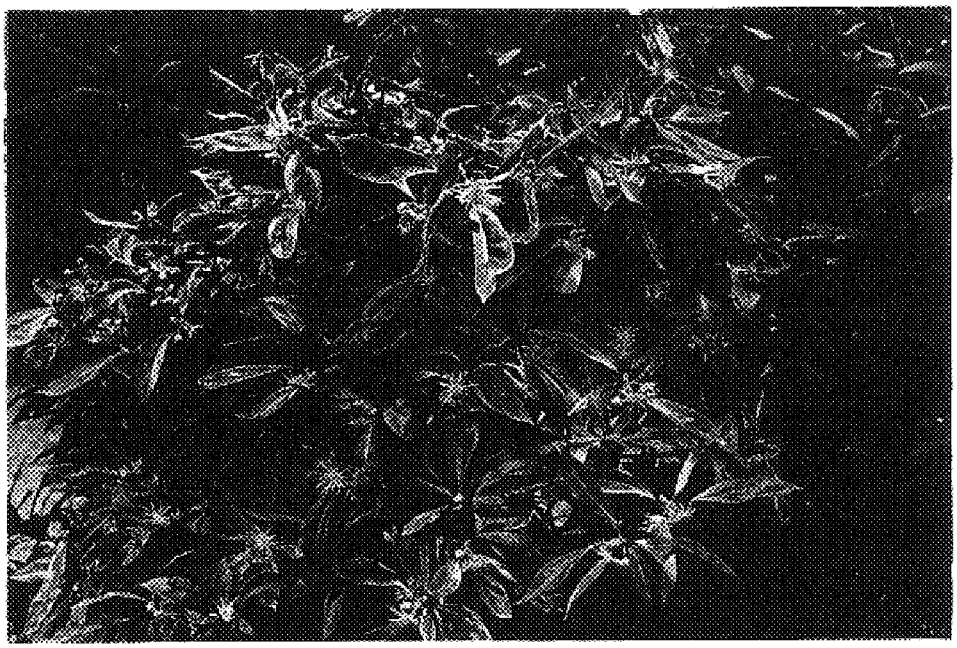
FIG. 4 is a photograph showing the plant.

The photographs of the drawing were taken Apr. 28, 1999 in Semmes, Ala. and illustrate the typical foliage form, with color as true as possible in this type of color photograph.

DETAILED DESCRIPTION OF THE INVENTION

The following observations, measurements and values describe plants of the new cultivar grown in Moncks Corner, S.C. in August, 1998. Color references are made in accordance with The Royal Horticultural Colour Chart of the British Color Council, except where general color terms of ordinary dictionary significance are obvious.

Origin:

Dodd & Dodd Nursery

Post Office Drawer 439

Semmes, Ala. 136575

Botanical classification: *Illicium floridanum.*

Parentage: Branch sport of *Illicium floridanum* 'Alba', variety 'Semmes'.

Commercial class: Ornamental; broad-leaf evergreen.

Propagation:

*Type cuttings.*—This plant has been asexually reproduced by means of semi-hardwood cuttings. All rooted cuttings have remained true to the new variety.

*Time to initiate root development.*—About 4 to 5 months.

Plant description:

*Form.*—Upright rounded shrub. Multi-trunked.

*Height.*—6 feet to 8 feet. Slightly shorter than the average for the species.

*Trunk diameter.*—Original plant — 3 inch diameter trunk.

*Tree diameter.*—2 foot diameter spread.

*Bark color.*—Brownish gray (RHS 199A), younger limbs dotted with varying numbers of small lenticels of color (RHS 199C); older limbs are without lenticels.

*Internodes length.*—About 2 to 3 inches.

Foliage:

*Type.*—Evergreen. Leaves mostly elliptic to lanceolate in shape. Apex acute to acuminate with leaf base cuneate.

*Arrangement.*—Alternate. In pseudo-whorls at end of stem.

*Leaf size.*—About 6.5–11 cm. long and 1.3–2.5 cm. wide.

*Leaf shape.*—Often asymmetrical. Entire.

*Texture.*—Leathery.

*Aspect.*—Smooth. Aromatic anise-like odor.

*Color.*—Variegated with the primary green of the leaves being a grey-green — Royal Horticultural Society 189A; variegated colors range from grey-green (RHS 188B) to yellow-green (RHS 144B) to yellow (RHS 3D), often with an admixture of the latter three colors.

*Vein color.*—Color RHS 190A.

*Venation pattern.*—Midrib evident but lateral veins not evident.

*Abaxial surface color of the observed leaf.*—Color RHS 189C.

*Leaf petiole.*—The length is about 1 to 2 cm.; the width is about 0.5 cm. and the color is RHS 191D.

Flower description:

*Locality where grown.*—Moncks Corner, S.C.

*Blooming habit.*—Has started to flower as early as late February in Moncks Corner and continued until mid-April. Peak times have been April 1$^{st}$, with a tendency to repeat in summer and fall.

*Continuity.*—Continuous.

*Borne.*—Singly on a ½"–1½" pedicel.

*Shape.*—Round, 1"–1½" in diameter.

*Fragrance.*—Reminiscent of a wet dog or fish.

Sepels:

*Number of sepals.*—6.

*Size of sepals.*—1 cm. long, ¼ cm. wide.

*Color.*—RHS66C.

*Flower.*—20–30 strap-shaped petals, soft pink, ligulate. Pollinated by a variety of insects.

*Arrangement.*—Single.

*Shape.*—Round.

*Texture.*—Thick, leathery.

*Aspect.*—Waxy.

*Size.*—1"–1½" in diameter.

*Color.*—Light pink (RHS66D) fading to softer pink (RHS69C).

*Pedicels.*—The diameter is 0.2 cm. and the color is RHS 149A.

Bud:

*Size.*—The bud is 1 cm. In length and ½ cm. in diameter.

*Shape.*—Globular with pointed tips. Rose-pink (RHS 60D).

*Color.*—Rose-pink (RHS 60D).

*Quantity of bloom.*—Abundant; outdoors.

*Peduncle.*—Length about ½"–1½".

Reproduction:

*Stamens.*—Number — 25–50.

*Pistil.*—Number — 11–21.

*Seed/fruit.*—One seeded, dehiscent follicles, 11–15 arranged in a whorl, ¾"–1" diameter, The seed capsule is first green (RHS 144C), then yellow (RHS 150A), and finally brown (RHS 199B), maturing in November. Has a star-like configuration, distinct, seeds BB-like, brown and shiney.

Resistance to disease/susceptibility: Resistance to disease has not been observed. The plant does not like full sun in the Southeastern U.S.

TABLE 1

*Illicium floridanum forma variegatum* and its relationship to wild *floridanum*.[1]

| | Wild *floridanum* | *Illicium floridanum forma variegatum* |
|---|---|---|
| LEAF LENGTH | 5–21 cm | 6.5–11 cm |
| LEAF WIDTH | 1.5–6 cm | 1.3–2.5 cm |
| LEAF SHAPE | Elliptic to lanceolate | Often asymmetrical |
| LEAF BASE | Cuneate | Narrowly cuneate |
| LEAF APEX | Acute to acuminate | Often curved |
| LEAF THICKNESS | Thin to leathery | Leathery |
| LEAF COLOR | Olive | Variegated |
| FLOWER COLOR | Maroon | Pink |

[1]Measurements for typical wild *I. floridanum* taken from Michael A. Vincent's treatment of *Illicium*, Pp. 59–61 In Flora of North America. 1997. Magnoliophyta: Magnoliidae and Hamemelidae. Volume 3. Oxford University Press. New York, Oxford. 590 p.

That which is claimed:

1. A new and distinct *Illicium* plant as herein described and illustrated.

* * * * *